United States Patent [19]

Nakakura et al.

[11] Patent Number: 5,703,080
[45] Date of Patent: Dec. 30, 1997

[54] METHOD FOR STABILIZING DUOCARMYCIN DERIVATIVES

[75] Inventors: Masashi Nakakura; Yuji Ueno; Eiji Hayakawa; Tokuyuki Kuroda, all of Shizuoka, Japan

[73] Assignee: Kyowa Hakko Kogyo Co., Ltd., Tokyo, Japan

[21] Appl. No.: 737,145

[22] PCT Filed: May 19, 1995

[86] PCT No.: PCT/JP95/00962

§ 371 Date: Oct. 30, 1996

§ 102(e) Date: Oct. 30, 1996

[87] PCT Pub. No.: WO95/31971

PCT Pub. Date: Nov. 30, 1995

[30] Foreign Application Priority Data

May 20, 1994 [JP] Japan ................... 6-106415

[51] Int. Cl.$^6$ .................. A61K 31/495; C07D 241/04
[52] U.S. Cl. ........................ 514/253; 544/373
[58] Field of Search ................. 514/253; 544/373

[56] References Cited

U.S. PATENT DOCUMENTS 5,070,092  12/1991  Kanda et al. .............. 514/253
5,326,753  7/1994  Ohtsuki et al. ............ 514/33

*Primary Examiner*—Joseph McKane
*Attorney, Agent, or Firm*—Fitzpatrick, Cella, Harper & Scinto

[57] ABSTRACT

Stabilized duocarmycin derivatives represented by formula (I):

wherein R is lower alkyl, allyl or benzyl, and X is Cl or Br, are prepared by adding at least a compound selected from the group consisting of a saccharide, an electrolyte, a water-soluble polymer, a polyhydric alcohol and a surfactant to a solution containing the duocarmycin derivatives. Also provided are freeze-dried pharmaceutical preparations containing the stabilized duocarmycin derivatives.

6 Claims, No Drawings

METHOD FOR STABILIZING DUOCARMYCIN DERIVATIVES

This application is a 371 of PCT/JP/95/00962 filed May 19, 1995.

TECHNICAL FIELD

The present invention relates to a method for the stabilization of duocarmycin derivatives and to preparations containing such stabilized derivatives.

BACKGROUND ART

Duocarmycin derivatives such as Compound A represented by the formula shown below are known to have anti-tumor activity (see U.S. Pat. No. 5,070,092). In addition, Compound A is known to be stabilized in its hydrobromide form (see European Patent No. A° 537575).

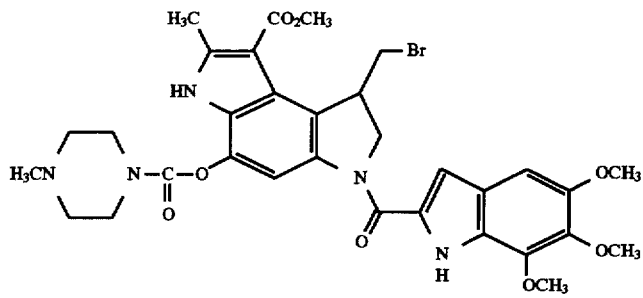

However, duocarmycin derivatives including Compound A in its hydrobromide form easily decompose in an aqueous solution. Thus, the instability of these compounds is a major problem in medications intended for long-term storage. Accordingly, a need exists for stable pharmaceutical preparations containing duocarmycin derivatives, which can be stored for a long period of time.

DISCLOSURE OF THE INVENTION

The present invention provides a method for stabilizing duocarmycin derivatives represented by general formula (I):

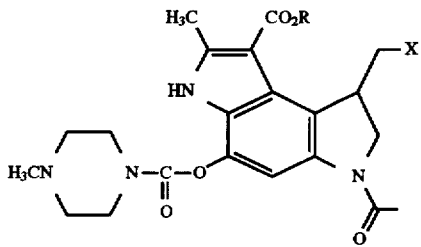

(I)

wherein R represents a lower alkyl group, an allyl group or a benzyl group, and X represents a chlorine atom or a bromine atom, which method is characterized in that at least one member selected from the group consisting of a saccharide, an electrolyte, a water-soluble polymer, a polyhydric alcohol and a surfactant is present in a solution containing said duocarmycin derivatives. Preferably, in the method for the stabilization, a solution containing said duocarmycin derivative represented by formula (I) and a saccharide is freeze-dried. More preferably, a solution further containing at least one member selected from the group Compound A consisting of an electrolyte, a water-soluble polymer, a polyhydric alcohol and a surfactant is freeze-dried. The present invention provides freeze-dried pharmaceutical preparations containing duocarmycin derivatives, which have been stabilized by the above-mentioned method.

In the definition of formula (I), the lower alkyl group means a straight chain or branched alkyl group having 1 to 6 carbon atoms, for example, a methyl group, an ethyl group, a propyl group, an isopropyl group, a butyl group, a sec-butyl group, a tert-butyl group, a pentyl group, and a hexyl group.

Duocarmycin derivatives represented by formula (I) can be produced by the method described in U.S. Pat. No. 5,070,092.

Specific examples of duocarmycin derivatives for use in the present invention are shown in Table 1.

TABLE 1

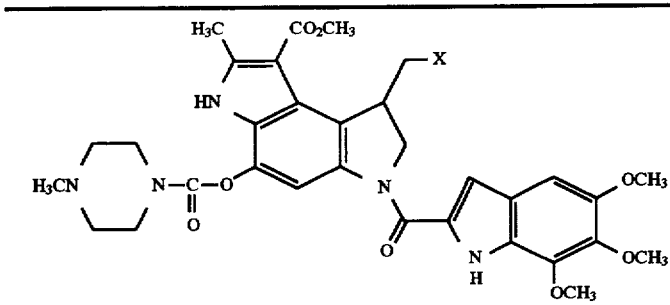

| Compound No. | X | IR (KBr), ν (cm⁻¹) |
|---|---|---|
| 1 (Compound A) | Br | 3475, 3232, 2944, 1698, 1491, 1410, 1313, 1217, 1110 |
| 1 (Compound A)* | Br | 1717, 1692, 1608, 1525, 1490, 1409, 1310, 1218, 1167, 1108 |
| 2 | Cl | 2940, 1698, 1637, 1491, 1410, 1314, 1218, 1154, 1109 |

*Hydrobromide monohydrate

In accordance with the present invention, a duocarmycin derivative represented by formula (I) and at least one member selected from the group consisting of a saccharide, an electrolyte, a water-soluble polymer, a polyhydric alcohol and a surfactant are dissolved in a solution, preferably an acidic solution, more preferably an acidic solution that has been adjusted to pH 5 or less. The resulting solution is filtered through a membrane filter under germ-free conditions and freeze-dried.

As the saccharide, lactose, sucrose, raffinose, dextran, etc. may be used. Preferred is lactose. The concentration of the saccharide in the solution is from 0.005 to 1000 mg/ml, preferably from 1 to 500 mg/ml. Any electrolyte which is pharmaceutically acceptable and which can increase the ionic strength of the solution can be employed. For instance, inorganic acids such as hydrochloric acid, hydrobromic acid, hydroiodic acid, sulfuric acid, carbonic acid, silicic acid, phosphoric acid, and boric acid; organic acids such as citric acid, and acetic acid; and their sodium salts, potassium salts, etc. may be used. The concentration of the electrolyte in the solution is from 0.001 to 500 mg/ml, preferably from 0.01 to 100 mg/ml. As the water-soluble polymer, polyvinyl alcohol, polyvinyl pyrrolidone, polyethylene glycol, carboxyvinyl polymer, etc. may be used at a concentration of 1 to 1000 mg/ml, preferably 10 to 500 mg/ml. As the polyhydric alcohol, glycerin, propylene glycol, etc. may be used at a concentration of 10 to 1000 mg/ml, preferably 100 to 500 mg/ml. As the surfactant, polyoxyethylene sorbitan fatty acid ester (Tween), polyoxyethylene-hydrogenated castor oil, etc. may be used at a concentration of 0.01 to 5000 mg/ml, preferably 0.1 to 500 mg/ml. The concentration of the duocarmycin derivative in the solution to be freeze-dried is from 0.001 to 1000 mg/ml, preferably from 0.1 to 10 mg/ml. Freeze-drying of the solution is carried out under appropriate conditions. For example, the solution is first frozen at −50° C. for 5 hours (pre-freezing), dried at −30° C. and at 0.05 mbar for 30 hours and then at 0° C. and at 0.05 mbar for 15 hours (primary drying). The material then further dried at 25° C. and at 0.05 mbar for 15 hours (secondary drying).

Typically, the solution is freeze-dried in a vial, and after freeze-drying, the vial containing the freeze-dried preparation is sealed with a rubber stopper and an aluminium cap, whereby a freeze-dried pharmaceutical preparation containing a duocarmycin derivative is obtained.

When clinically using duocarmycin freeze-dried preparations, the freeze-dried pharmaceutical preparation is dissolved in a solution containing as a stabilizer at least one member selected from the group consisting of an electrolyte, a water-soluble polymer, a polyhydric alcohol and a surfactant.

The pharmaceutical preparation of the present invention may contain as may be appropriate an antioxidant, an antiseptic, a buffer, a soothing agent, a solubilizer, an isotonicity agent, a preservative, a stabilizer, a vehicle, a binder, a disintegrator, a wetting agent, a lubricant, a coloring agent, an aromatic, a flavoring agent, a coating, a suspending agent, an emulsifier, a plasticizer, a surfactant, and the like which are pharmaceutically acceptable. For instance, the preparation may additionally be formulated to contain an antioxidant such as ascorbic acid, vitamin E, butylhydroxytoluene and benzylhydroxytoluene; an antiseptic such as parabens and chlorobutanol; a buffer such as phosphoric acid and citric acid; a soothing agent such as benzyl alcohol and lidocaine; a vehicle such as crystalline cellulose, hydroxypropyl starch, starch and corn starch; a binder such as pullulan, polyvinyl alcohol and hydroxypropyl cellulose; a disintegrator such as carboxymethyl cellulose and croscarmellose sodium; a lubricant such as magnesium stearate, talc and hydrogenated oil, etc.

The pharmaceutical preparation of the present invention may be made not only as injectable preparations, but also as oral preparations such as tablets, capsules and granules, as well as for rectal administration in the form of suppositories, etc.

The dose and administration schedule of the pharmaceutical preparation of the present invention for use as an anti-tumor agent will vary depending on various factors such as the patient's age, weight and physical condition. For instance, when the preparation is used as an anti-tumor injection, it is suitable to administer the active compound in an amount of 0.0001 to 10 mg/kg. Administration may be made once a day (single administration or consecutive administration) or intermittently once to three times a week or once every three weeks.

Certain specific embodiments of the invention are illustrated by the following representative examples and test examples.

Best Mode for Carrying Out the Invention

Example 1

In this example, 50 mg of citric acid, 100 mg of Compound A hydrobromide and 5000 mg of lactose were dissolved in distilled water to make a total volume of 200 ml. The resulting solution was put into 15-ml glass vials, in 2 ml portions, and freeze-dried under reduced pressure. After freeze-drying, the pressure was restored to normal pressure in a nitrogen stream, and each vial was sealed with a rubber stopper and an aluminium cap to yield a freeze-dried preparation containing Compound A.

Example 2

In this example, 50 mg of citric acid, 100 mg of Compound A hydrobromide, 5000 mg of lactose and 100 mg of sodium bromide were dissolved in distilled water to make a total volume of 200 ml. The resulting solution was put into 15-ml glass vials, in 2 ml portions, and freeze-dried under reduced pressure. After freeze-drying, the pressure was restored to normal pressure in a nitrogen stream, and each vial was pealed with a rubber stopper and an aluminium cap to yield a freeze-dried preparation containing Compound A.

Example 3

In this example, 50 mg of citric acid, 100 mg of Compound A hydrobromide, 5000 mg of lactose, 100 mg of sodium bromide and 500 mg of polyoxyethylene sorbitan monooleate (Tween 80) were dissolved in distilled water to make a total volume of 200 ml. The resulting solution was put into 15-ml glass vials, in 2 ml portions, and freeze-dried under reduced pressure. After freeze-drying, the pressure was restored to normal pressure in a nitrogen stream, and each vial was sealed with a rubber stopper and an aluminium cap to yield a freeze-dried preparation containing Compound A.

Example 4

In this example, 50 mg of citric acid and 100 mg of Compound A hydrobromide were dissolved in distilled water to make a total volume of 200 ml. The resulting solution was put into 15-ml glass vials, in 2 ml portions, and freeze-dried under reduced pressure. After freeze-drying, the pressure was restored to normal pressure in a nitrogen stream, and each vial was sealed with a rubber stopper and an aluminium cap to yield a freeze-dried preparation containing Compound A.

Test Example 1

Compound A hydrobromide (1 mg) was dissolved in distilled water to make a total volume of 10 ml (control solution). Separately, 0.5 mg of citric acid and 1 mg of Compound A hydrobromide were dissolved in distilled water together with 1 mg of sodium bromide (Test Solution 1), or 1 mg of sodium bromide and 5 mg of Tween 80 (Test Solution 2) to make a total volume of 10 ml. All solutions tested had a pH adjusted to 3.6. The control solution and the test solutions were respectively put into 15-ml glass vials, and stored in a thermostat at 25° C. Each solution was sampled in an amount of 1 ml at predetermined intervals. The content of Compound A remaining in each of the test sample solutions was analyzed by high performance liquid chromatography and the results are shown in Table 2.

Conditions for High Performance Liquid Chromatography

Column: Inertsil ODS-2, 6.0ϕ×250 mm

Mobile Phase: 0.05M phosphate buffer (pH 5.9)/ acetonitrile (48 parts by volume/52 parts by volume)

Flow Rate: 1.0 ml/min

Detection Wavelength: 330 nm

TABLE 2

Stability of Compound A in Aqueous Solution (at 25° C.)

| Test Solution | Content of Compound A (%) | | |
|---|---|---|---|
| | 0 hour (start) | 2 hours | 4 hours |
| Control Solution | 100.0 | 95.5 | 91.9 |
| Test Solution 1 | 100.0 | 95.7 | 93.2 |
| Test Solution 2 | 100.0 | 98.6 | 97.9 |

As is seen from the results of the control solution in Table 2, Compound A decomposes in an aqueous solution with the passage of time. The stability of Compound A in an aqueous solution was improved by adding thereto sodium bromide alone (Test Solution 1) or with sodium bromide and Tween 80 (Test Solution 2). From these results, it is evident that the addition of sodium bromide or sodium bromide and Tween 80 to an aqueous solution of Compound A improves the stability of Compound A in solution during the preparation process of a freeze-dried preparation and during the period between the reconstitution of the freeze-dried preparation and the administration of the reconstituted preparation to a patient. Thus, the probability of introducing a decomposition product of Compound A to the patient is reduced.

Test Example 2

Citric acid (5 mg) and 1 mg of Compound A hydrobromide were dissolved in distilled water together with 1 g of propylene glycol (Test Solution 3) or 1 g of polyethylene glycol 400 (Test Solution 4) to make a total volume of 10 ml. Both solutions had a pH adjusted to 3.0. The test solutions were respectively put into 15-ml glass vials, and stored in a thermostat at 40° C. Each solution was sampled in an amount of 1 ml at predetermined intervals. The content of Compound A remaining in each of the test sample solutions was analyzed by high performance liquid chromatography and the results are shown in Table 3.

Conditions for High Performance Liquid Chromatography

Column: Inertsil ODS-2, 6.0ϕ×250 mm

Mobile Phase: 0.05M phosphate buffer (pH 5.9)/ acetonitrile (48 parts by volume/52 parts by volume)

Flow Rate: 1.0 ml/min

Detection Wavelength: 330 nm

TABLE 3

Stability of Compound A in Aqueous Solution (at 40° C.)

| Test Solution | Content of Compound A (%) | | |
|---|---|---|---|
| | 0 hour (start) | 3 hours | 6 hours |
| Test Solution 3 | 100.0 | 68.4 | 46.8 |
| Test Solution 4 | 100.0 | 84.9 | 70.8 |

Test Example 3

The freeze-dried preparations obtained in Examples 1 to 4 were stored in a thermostat at 60° C. for 30 days. The content of Compound A remaining in each of these preparations was analyzed by high performance liquid. Chromatography. The results are shown in Table 4.

TABLE 4

Storage Stability of Compound A (at 60° C., 30 days)

| Example No. | Content of Compound A (%) |
|---|---|
| Example 1 | 100.0 |
| Example 2 | 100.4 |
| Example 3 | 99.3 |
| Example 4 | 97.6 |

As is apparent from the results given in Table 4, the stability of the freeze-dried preparations containing Compound A was improved by the addition of the saccharide.

Industrial Applicability

The present invention provides a method for the stabilization of duocarmycin derivatives and preparations containing them.

We claim:

1. A method for stabilizing a compound, comprising the steps of;

selecting a compound represented by formula (I):

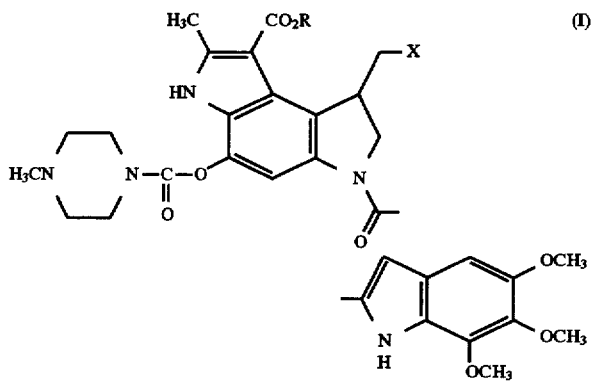

wherein R represents a straight chain or branched alkyl group having 1 to 6 carbon atoms, an allyl group of a benzyl group, and x represents a chlorine atom or a bromine atom; and preparing a solution of said compound and at least one material selected from the group consisting of a saccharide, an electrolyte, a water-soluble polymer, a polyhydric alcohol and a surfactant.

2. The method according to claim 1, wherein the solution contains said saccharide, and said method further comprises a step of freeze-drying said solution containing said compound and said saccharide.

3. The method according to claim 2, wherein prior to freeze-drying the solution also contains at least one additional material selected from the group consisting of an electrolyte, a water-soluble polymer, a polyhydric alcohol and a surfactant.

4. A pharmaceutical composition which comprises a compound represented by formula (I):

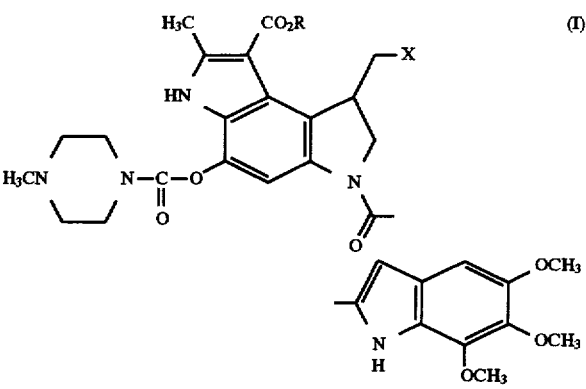

which is obtained by freeze-drying an acidic solution containing the compound and at least one material selected from the group consisting of a saccharide, an electrolyte, a water-soluble polymer, a polyhydric alcohol and a surfactant.

5. The freeze-dried pharmaceutical composition according to claim 4, wherein the solution contains the compound and said saccharide prior to freeze-drying.

6. The freeze-dried pharmaceutical composition according to claim 5, wherein prior to freeze-drying the solution also contains at least one material selected from the group consisting of an electrolyte, a water-soluble polymer, a polyhydric alcohol and a surfactant.

* * * * *

UNITED STATES PATENT AND TRADEMARK OFFICE
CERTIFICATE OF CORRECTION

PATENT NO. : 5,703,080

DATED : December 30, 1997

INVENTOR(S) : MASASHI NAKAKURA ET AL.

It is certified that error appears in the above-identified patent and that said Letters Patent is hereby corrected as shown below:

COLUMN 1

Line 18, "A°" should read --A--.

COLUMN 3

Line 58, "then" should read --is then--.

COLUMN 5

Line 17, "pealed" should read --sealed--.

COLUMN 7

Line 1, ". 10" should be deleted.
   Line 23, "of;" should read --of:--.
   Line 42, "of" should read --or--.
   Line 43, "x" should read --X--.

Signed and Sealed this

Eighteenth Day of August, 1998

Attest:

BRUCE LEHMAN

Attesting Officer     Commissioner of Patents and Trademarks